United States Patent [19]

Rauleder et al.

[11] Patent Number: 5,468,705
[45] Date of Patent: Nov. 21, 1995

[54] STORAGE-STABLE SOLUTION OF CARBONATED MAGNESIUM METHOXIDE IN METHANOL AND ITS USE

[75] Inventors: Hartwig Rauleder; Burkhard Standke; Hans-Joachim Kötzsch; Reinhold Schork, all of Rheinfelden, Germany

[73] Assignee: Huels Aktiengesellschaft, Marl, Germany

[21] Appl. No.: 167,353

[22] Filed: Dec. 15, 1993

[30] Foreign Application Priority Data

Jan. 7, 1993 [DE] Germany .................. 43 00 186.6

[51] Int. Cl.$^6$ .................. C07F 3/02; D21H 17/12; D21H 25/02; B01J 31/12
[52] U.S. Cl. .................. 502/151; 502/152; 502/156; 502/171; 502/172; 427/439; 106/287.23; 252/380; 252/397; 252/399; 252/400.61
[58] Field of Search .................. 427/421, 430.1, 427/439; 252/380, 397, 399, 400.1, 400.61; 502/151, 152, 156, 171, 172; 106/287.23

[56] References Cited

U.S. PATENT DOCUMENTS

| | | | |
|---|---|---|---|
| 3,939,091 | 2/1976 | Kelly, Jr. .................. | 252/189 |
| 3,969,549 | 7/1976 | Williams et al. .................. | 427/248 |
| 4,318,963 | 3/1982 | Smith .................. | 428/537 |
| 4,540,679 | 9/1985 | Arzoumanidis et al. .................. | 502/111 |
| 4,860,685 | 8/1989 | Smith .................. | 427/421 |
| 4,866,022 | 9/1989 | Arzoumanidis et al. .................. | 502/120 |
| 4,988,656 | 1/1991 | Arzoumanidis et al. .................. | 502/127 |
| 5,013,702 | 5/1991 | Arzoumanidis et al. .................. | 502/120 |
| 5,104,997 | 4/1992 | Kamienski et al. .................. | 427/430.1 |
| 5,208,072 | 5/1993 | Kamienski et al. .................. | 427/439 |
| 5,210,334 | 5/1993 | Standke et al. .................. | 568/851 |
| 5,227,542 | 7/1993 | Horns et al. .................. | 568/851 |
| 5,322,558 | 6/1994 | Wittekind et al. .................. | 106/287.23 |

FOREIGN PATENT DOCUMENTS

| | | |
|---|---|---|
| 0159150 | 10/1985 | European Pat. Off. . |
| 0236082 | 9/1987 | European Pat. Off. . |
| 0285227 | 10/1988 | European Pat. Off. . |
| 0436801 | 7/1991 | European Pat. Off. . |
| 0491128 | 6/1992 | European Pat. Off. . |

OTHER PUBLICATIONS

Reagents For Organic Synthesis, pp. 631–633, L. F. Fieser, et al., "Magnesium Methyl Carbonate (MMC), CH3OMgOCO2CH3+XCO2" (No Date).

Primary Examiner—Asok Pal
Assistant Examiner—Walter D. Griffin
Attorney, Agent, or Firm—Oblon, Spivak, McClelland, Maier & Neustadt

[57] ABSTRACT

The present invention relates to a storage-stable solution of carbonated magnesium methoxide of the formula $Mg(CH_3O)_2 (CO_2)_n$ in methanol, and processes for their preparation by reacting metallic magnesium with methanol and $CO_2$ or reacting magnesium methoxide in methanol with $CO_2$, wherein the magnesium content of the solution is from 0.1 to 8% by weight, based on the total weight of the solution, and the $CO_2$ content n is from 1 to 2.2. The present solution is used, inter alia, for the preservation of paper or for the preparation of a catalyst for the polymerization of olefins.

5 Claims, No Drawings

5,468,705

STORAGE-STABLE SOLUTION OF CARBONATED MAGNESIUM METHOXIDE IN METHANOL AND ITS USE

BACKGROUND OF THE INVENTION

1. Field of the Invention

The present invention relates to a storage-stable solution of carbonated magnesium methoxide of the formula $Mg(CH_3O)_2 (CO_2)_n$ in methanol, a process for the preparation of a storage-stable solution of carbonated magnesium methoxide of the formula $Mg(CH_3O)_2 (CO_2)_n$ in methanol by reacting metallic magnesium with methanol and $CO_2$, and to a process for the preparation of a storage-stable solution of carbonated magnesium methoxide of the formula $Mg(CH_3O)_2 (CO_2)_n$ in methanol by reacting magnesium methoxide in methanol with $CO_2$. The present invention also relates to a method of preserving paper and a method of preparing a catalyst for the polymerization of olefins using a storage-stable solution of carbonated magnesium methoxide in methanol.

2. Discussion of the Background

Magnesium alcoholates (or alkoxides) are, as a rule, not very soluble in the corresponding alcohols. In some cases, magnesium alcoholates are virtually insoluble in the corresponding alcohols. An exception is magnesium methoxide, which has a solubility of up to about 12% by weight in methanol.

A technically simple method for increasing the solubility of magnesium alcoholates is carbonation. Gaseous, liquid or solid $CO_2$ is introduced into a suspension of the magnesium alcoholate in the corresponding alcohol. A soluble $CO_2$ adduct forms. In the case of magnesium ethoxide, the $CO_2$ adduct is soluble up to a concentration of more than 30% by weight in ethanol, whereas pure magnesium ethoxide is virtually insoluble in ethanol.

Alcohol-soluble carbonated magnesium alkoxides are widely used. Thus, for example, magnesium alkoxides brought into solution by carbonation can be used in the long-term preservation of paper, in particular books, and can be substituted for the zinc alkyls which are likewise used for this purpose according to U.S. Pat. No. 3,969,549, EP-A 0,285,227, U.S. Pat. No. 4,318,963 and U.S. Pat. No. 3,939,091, but which present problems during use.

According to European Patent 0,159,150 and European Patent 0,236,082, a further field of use is the preparation of catalysts for the polymerization of olefins. For example, spherical magnesium methoxide and magnesium ethoxide are useful for this purpose. Spherical magnesium methoxide and magnesium ethoxide can be prepared, for example, by spray drying or precipitation of carbonated magnesium methoxide solutions or magnesium ethoxide solutions, and, if required, subsequent decarbonation.

It is known in principle that solutions of carbonated magnesium alcoholates can be prepared according to the two reaction schemes below. On the one hand, metallic magnesium can be reacted with an alcohol ROH and $CO_2$ (equation (1)). On the other hand, a magnesium alkoxide can be reacted with $CO_2$ (equation (2)):

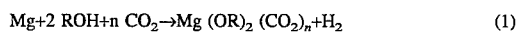
(1)

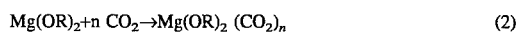
(2)

Here, R denotes an alkyl group, preferably a branched or linear $C_1$–$C_4$ alkyl group.

European Patent 0,236,082 teaches the preparation of carbonated magnesium alkoxides by reacting magnesium alkoxides with $CO_2$ in a solvent. Preferred solvents are alcohols. For example, the preparation of carbonated magnesium ethoxide by reacting magnesium ethoxide with $CO_2$ in ethanol as a solvent is disclosed.

In "Reagents for Organic Synthesis" vol. 1 page 631, Fieser et al describe the preparation of carbonated magnesium methoxide by two different routes. In one procedure, a suspension of magnesium methoxide in methanol is reacted with $CO_2$. In the other, magnesium turnings are reacted with methanol to give magnesium methoxide. After the methanol has been partially stripped off at 50° C. and reduced pressure, dimethylformamide is added as a solvent and $CO_2$ is passed into this solution. The remaining methanol is distilled off, and a slightly yellow solution of carbonated magnesium methoxide in dimethylformamide is obtained.

European Patent 0,159,150 reports on the use of solutions of carbonated magnesium alcoholates in alcohols for the preparation of active catalyst carriers for olefin polymerization. The solutions used contain 10 to 80% by weight of magnesium alcoholate, and 0.1 to 4 mol of $CO_2$ per mol of magnesium and are prepared by reacting magnesium alcoholate, dispersed in alcohol, with gaseous $CO_2$.

However, the alcoholic solutions of carbonated magnesium alkoxides according to these references must be used within a short period of time, since discoloration, precipitation and gel formation can occur after only a few days, even on storage in tightly sealed vessels.

The industrial use of such solutions is considerably limited. On the one hand, colored solutions cannot be used, for example, for the long-term preservation of books. On the other hand, solutions in which there is a danger of uncontrolled precipitation cannot be used for the preparation of catalysts based on magnesium alkoxide.

SUMMARY OF THE INVENTION

Accordingly, one object of the present invention is to provide a novel storage-stable solution of carbonated magnesium methoxide, which remains virtually colorless even over a relatively long period of time, and exhibits neither precipitation nor gel formation.

As a result of establishing defined magnesium and $CO_2$ concentrations in a solution of carbonated magnesium methoxide in methanol, according to the present invention, it has surprisingly been found that discoloration, precipitation and gel formation do not occur even during storage over long periods of time.

DETAILED DESCRIPTION OF THE PREFERRED EMBODIMENT

The present invention therefore relates to a storage-stable solution of carbonated magnesium methoxide of the formula $Mg(CH_3O)_2 (CO_2)_n$ in methanol, wherein the magnesium content of the solution is from 0.1 to 8% by weight, based on the total solution, and the $CO_2$ content n is from 1 to 2.2. Preferably, the present storage-stable solution has a magnesium content of from 1 to 8% by weight, and more preferably, from 3 to 7.5% by weight, based on the total weight of the solution. Preferably, the present storage-stable solution has a $CO_2$ content n of from 1.1 to 2.1, and more preferably, from 1.13 to 2.02.

The present invention furthermore relates to a process for the preparation of a storage-stable solution of carbonated magnesium methoxide of the formula $Mg(CH_3O)_2 (CO_2)_n$ in methanol, by reacting metallic magnesium with methanol and $CO_2$, and adjusting the magnesium content of the solution to a value of from 0.1 to 8% by weight, based on the total weight of the solution, and the $CO_2$ content to a value n of from 1 to 2.2.

The present invention also concerns a process for the preparation of a storage-stable solution of carbonated magnesium methoxide of the formula $Mg(CH_3O)_2 (CO_2)_n$ in methanol, by reacting magnesium methoxide in methanol with $CO_2$, and adjusting the magnesium content of the solution to a value of from 0.1 to 8% by weight, based on the total weight of the solution, and the $CO_2$ content to a value n of from 1 to 2.2.

The present solution can also be made directly, without the need for an adjusting step. Accordingly, the present invention also concerns processes for the preparation of a storage-stable solution of carbonated magnesium methoxide of the formula $Mg(CH_3O)_2 (CO_2)_n$ in methanol, by either (A) reacting an amount of metallic magnesium with amounts of methanol and $CO_2$ sufficient to produce a solution having a magnesium content of from 0.1 to 8% by weight, based on the total weight of the solution, and a $CO_2$ content n of from 1 to 2.2, or (B) reacting an amount of magnesium methoxide in an amount of methanol with an amount of $CO_2$ sufficient to produce a solution having a magnesium content of from 0.1 to 8% by weight, based on the total weight of the solution, and a $CO_2$ content to a value n of from 1 to 2.2.

The present invention also relates to the use of the present storage-stable solution of carbonated magnesium methoxide in methanol for the preservation of paper, and to the use of the present storage-stable solution of carbonated magnesium methoxide in methanol for the preparation of a catalyst for the polymerization of olefins.

In the preparation of the present solution of carbonated magnesium methoxide, either metallic magnesium (see equation (1) above) or magnesium methoxide (see equation (2) above) serves as the magnesium source. The use of metallic magnesium is economically more advantageous. For example, magnesium methoxide is usually obtained from magnesium metal by reaction with methanol. Therefore, a reaction step is dispensed with when metallic magnesium is used. Furthermore, products of higher color quality can be produced in the reaction of metallic magnesium with methanol and $CO_2$ according to equation (1). Thus, in the reaction of metallic magnesium with methanol and $CO_2$, solutions according to the present invention are obtained which have slightly lower color numbers, measured according to the Gardner method of measurement, compared with solutions prepared from magnesium methoxide and $CO_2$ according to equation (2).

In the reaction of metallic magnesium with methanol and $CO_2$, the surface of the magnesium is continuously exposed due to the solubility of the carbonated magnesium methoxide. Therefore, no passivation of the metal surface occurs as a result of the formation of an insoluble boundary layer between metal and methanol. In the context of the present application, "passivation" refers to reaction of the metal with an oxidizing agent, which may result in inactivation of the metal surface.

In the preparation of the present solution in accordance with equation (1), it is therefore not necessary to rely on the use of surface-rich magnesium material, such as magnesium turnings or magnesium granules, which is required, for example, in the industrial production of magnesium methoxide. Instead, magnesium block material, which is cheaper and easier to handle in terms of safety, can be used.

Furthermore, no auxiliaries, such as, for example, mercury salts (cf. *Liebigs Annalen der Chemie*, 444, 236, 1925), are required for initiating the reaction. Therefore, the achievable product purity is slightly greater when magnesium metal is used in accordance with equation (1), as compared with that obtained when magnesium methoxide is used in accordance with equation (2).

Carbonation can be effected by passing gaseous $CO_2$ into, or by adding liquid or solid $CO_2$ to, the reaction mixture of methanol and magnesium according to equation (1), or the reaction mixture of methanol and magnesium methoxide according to equation (2).

The $CO_2$ content n of the solution according to the present invention can thus be adjusted or regulated by metering gaseous, liquid or solid $CO_2$ into the mixture. In the context of the present application, "metering" refers to adding a measured amount of $CO_2$ into the reaction mixture, sufficient to produce a solution having a $CO_2$ content n of from 1 to 2.2.

In another variant, the $CO_2$ content n of the present solution can be adjusted by thermally expelling $CO_2$ from a solution of carbonated magnesium methoxide in methanol which contains an excess of $CO_2$. Preferably, "thermally expelling" refers to heating a solution of carbonated magnesium methoxide containing an excess of $CO_2$ at a temperature, under a reduced pressure and for a length of time sufficient to provide a $CO_2$ content n of from 1.0 to 2.2.

Thermal expulsion may be conveniently conducted using a rotary evaporator. Suitable temperatures may include a bath or "bottom" temperature of from 10° C. to 60° C., more preferably from 20° C. to 40° C. Suitable pressures may include a reduced pressure of from 500 mbar to 25 mbar absolute, more preferably from 250 mbar to 90 mbar absolute.

The amount of $CO_2$ introduced can be easily monitored via the mass balance, through the weight increase of the solution after addition of $CO_2$. The magnesium concentration of the present solution can be adjusted in a simple manner by distilling off methanol from a solution of carbonated magnesium methoxide in methanol, or by metering a predetermined amount of methanol into a solution of carbonated magnesium methoxide in methanol, sufficient to provide a magnesium content of from 0.1 to 8% by weight of the solution. The magnesium content of the solution is preferably adjusted by distilling excess methanol from a solution of carbonated magnesium methoxide in methanol.

Owing to the sensitivity of the solution to hydrolysis and to oxidation, all operations must be carried out in the absence of air and moisture.

The present invention also concerns a method for preserving paper, comprising applying a solution of carbonated magnesium methoxide of the formula $Mg(CH_3O)_2 (CO_2)_n$ in methanol, wherein the magnesium content of the solution is from 0.1 to 8% by weight, based on the total weight of the solution, and the $CO_2$ content n is from 1 to 2.2, to the paper. The solution can be applied to paper by any known method; for example, by dipping the paper into or passing the paper through the solution, or by spraying the solution onto the paper. The present solution may be diluted, preferably with methanol, prior to application to the paper.

The present invention also concerns a method for preparing a catalyst for the polymerization of olefins, comprising forming spherical magnesium methoxide from a solution of carbonated magnesium methoxide of the formula $Mg(CH_3O)_2 (CO_2)_n$ in methanol, wherein the magnesium content of the solution is from 0.1 to 8% by weight, based on the total weight of the solution, and the $CO_2$ content n is from 1 to 2.2. The spherical magnesium methoxide can be prepared by conventional methods; for example, by spray drying the present carbonated magnesium methoxide solution, or precipitating carbonated magnesium methoxide from the present solution, to form a solid magnesium methoxide. If required, the solid magnesium methoxide may be subsequently decarbonated by methods known in the art, such as heating (for example, to a temperature of from 20° C. to 200° C.) under vacuum.

Solutions of carbonated magnesium methoxide in methanol having an excessively high magnesium concentration, i.e., having a magnesium concentration greater than about 8.9% by weight, tend to exhibit precipitation or gel formation. Surprisingly, the tendency for precipitates to crystallize out or for gel formation to occur is not so strongly dependent on the amount of $CO_2$ used for the carbonation, in contrast to solutions of carbonated magnesium ethoxide in ethanol. Thus, for example, it is possible to prepare a solution according to the present invention which comprises magnesium methoxide in methanol, is stable to precipitation and has a magnesium content of more than 5% by weight and a $CO_2$ content n of more than 2. In the case of a solution of carbonated magnesium ethoxide in ethanol, a precipitate crystallizes out in a few weeks at the same magnesium and $CO_2$ concentrations.

Also surprising is the fact that, in the case of the present solution of carbonated magnesium methoxide in methanol, a $CO_2$ content n of 1 to 1.2 does not lead to coloration on storage within weeks. By contrast, in the case of solutions of carbonated magnesium ethoxide in ethanol, such a low $CO_2$ content may lead to coloration.

If the magnesium concentration is adjusted to a value of from 0.1 to 8% by weight and the $CO_2$ content n to a value of from 1 to 2.2, one obtains the present solution, which is stable to precipitation and color changes.

Ethanolic solutions of carbonated magnesium ethoxide having a magnesium content of 3.6% by weight, prepared by carbonation of commercially available magnesium ethoxide (standard particles, manufacturer: Hüls AG) in ethanol, have a color number of 2–3 (measured according to "Gardner") shortly after their preparation. On the other hand, surprisingly, color numbers of not more than 2 (measured according to "Gardner") are obtained at the same concentration for the present solution, prepared by carbonation of magnesium methoxide in methanol.

If, instead of magnesium methoxide, magnesium block material is used as starting material for the preparation, color numbers of <1 (measured according to "Gardner") are obtained for a solution having the same magnesium and $CO_2$ concentrations. Thus, if metallic magnesium is used as the magnesium source for the preparation of the present solution, slightly better products are obtained in terms of purity and color quality, than when magnesium methoxide is used as a starting material.

Other features of the invention will become apparent in the course of the following descriptions of exemplary embodiments which are given for illustration of the invention and are not intended to be limiting thereof.

Example 1

Preparation of a storage-stable solution of carbonated magnesium methoxide having a high $CO_2$ content from magnesium methoxide and $CO_2$ in methanol 470 g of methanol are placed in a 1 l three-necked flask equipped with a reflux condenser, a gas inlet tube, a nitrogen blanketing system and a KPG blade stirrer, and 135 g of magnesium methoxide (manufacturer: Hüls AG) are then added, while blanketing the reaction system with nitrogen. $CO_2$ is passed in while stirring. The $CO_2$ absorption is monitored continuously by checking the weight of the solution. The temperature in the reaction space increases continuously. The reaction is terminated on absorption of 139 g of $CO_2$, corresponding to a $CO_2$ content n of 2.02. The temperature reaches a maximum value of 64° C. The solution thus produced is slightly yellow and has a color number of 1 to 2 (measured according to "Gardner") and a magnesium content of 5.1% by weight. No coloration, precipitation or gel formation occurs after storage for 6 weeks in a tightly sealed glass bottle.

Example 2

Preparation of a storage-stable solution of carbonated magnesium methoxide having a low $CO_2$ content from magnesium methoxide and $CO_2$ in methanol 470 g of methanol are placed in a 1 l three-necked flask equipped with a reflux condenser, a gas inlet tube, a nitrogen blanketing system and a KPG blade stirrer, and 135 g of magnesium methoxide (manufacturer: Hüls AG) are then added while blanketing the reaction system with nitrogen. $CO_2$ is passed in while stirring. The $CO_2$ absorption is monitored continuously by checking the weight of the solution. The temperature in the reaction space increases continuously. The reaction is terminated on absorption of 78 g of $CO_2$, corresponding to a $CO_2$ content n of 1.13. The temperature reaches a maximum value of 64° C. The solution thus produced is slightly yellow and has a color number of 1 to 2 (measured according to "Gardner") and a magnesium content of 5.5% by weight. No coloration, precipitation or gel formation occurs after storage for 6 weeks in a tightly sealed glass bottle.

Example 3 (Comparative Example)

In order to establish a higher magnesium concentration, 500 g of the solution from Example 1 are evaporated down over a period of about 1.5 hours in a rotary evaporator, at a bottom temperature increasing from 20° to 30° C. and at a pressure decreasing from 220 to 75 mbar absolute. During this procedure, the solution loses about 38 g of $CO_2$ and 150 g of methanol. The $CO_2$ content n of the viscous solution is 1.19 and the magnesium content is 8.9% by weight. After storage for about 4 days, a precipitate initially crystallizes out. After about 3 weeks, the solution gels completely.

Example 4

Preparation of a storage-stable solution of carbonated magnesium methoxide having a high magnesium content from magnesium methoxide and $CO_2$ in methanol In order to establish a higher magnesium concentration, 500 g of the solution from Example 1 are evaporated down over a period of about 1 hour in a rotary evaporator at a bottom temperature increasing from 20 to 30° C. and at a pressure decreasing from 220 to 120 mbar absolute. During this procedure, the solution loses about 35 g of $CO_2$ and 125 g of methanol. The $CO_2$ content n of the viscous solution is 1.26 and the magnesium content is 7.5% by weight. No coloration, precipitation or gel formation occurs after storage for 6 weeks in a tightly sealed glass bottle.

Example 5

Preparation of a storage-stable solution of carbonated magnesium methoxide from metallic magnesium and $CO_2$ in methanol 2,000 g of methanol are placed in a 4 l double-jacketed three-necked flask equipped with a reflux condenser, a gas inlet tube, a nitrogen blanketing system and a KPG blade stirrer, and 142 g of magnesium block material (manufacturer: Normag) which has been sawn to an edge length of 9 cm×2 cm×2 cm are then suspended, while blanketing with nitrogen, in the reaction apparatus by means of stainless steel wire so that it is completely immersed in methanol. $CO_2$ is passed in while stirring. The $CO_2$ absorption is monitored continuously by checking the weight of the solution. A gentle reflux is established by means of thermostatting. After the absorption of 436 g of $CO_2$, corresponding to a $CO_2$ content n of 1.75, the magnesium has dissolved with evolution of hydrogen. The magnesium content of the solution is 5.5% by weight. The resulting solution is clear and has a color number of <1 (measured according to "Gardner"). No coloration, precipitation or gel formation occurs after storage for 6 weeks in a tightly sealed glass bottle.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States in:

1. A storage-stable solution of carbonated magnesium methoxide of the formula $Mg(CH_3O)_2 (CO_2)_n$ in methanol, wherein the magnesium content of the solution is from 3 to 8% by weight, based on the total weight of the solution, and the $CO_2$ content n is from 1.13 to 2.2.

2. The solution of claim 1, wherein the magnesium content of the solution is from greater than 5 to 8% by weight.

3. The solution of claim 1, wherein the magnesium content of the solution is from 5.1 to 7.5% by weight, the $CO_2$ content n is from 1.13 to 2.02 and no coloration, precipitation or gel formation occurs in said solution after storage for six weeks in a sealed glass bottle.

4. A method of preserving paper, comprising applying a storage-stable solution of carbonated magnesium methoxide of the formula $Mg(CH_3O)_2 (CO_2)_n$ in methanol, wherein the magnesium content of the solution is from 3 to 8% by weight, based on the total weight of the solution, and the $CO_2$ content n is from 1.13 to 2.2, to paper.

5. A method of preparing a catalyst for the polymerization of an olefin, comprising forming spherical magnesium methoxide from a storage-stable solution of carbonated magnesium methoxide of the formula $Mg(CH30)_2 (CO_2)_n$ in methanol, wherein the magnesium content of the solution is from 3 to 8% by weight, based on the total weight of the solution, and the $CO_2$ content n is from 1.13 to 2.2.

* * * * *